US009095140B2

(12) United States Patent
Seitz et al.

(10) Patent No.: US 9,095,140 B2
(45) Date of Patent: *Aug. 4, 2015

(54) USE OF DITHIINE-TETRACARBOXIMIDES FOR CONTROLLING PHYTOPATHOGENIC FUNGI

(71) Applicant: Bayer Intellectual Property GmbH, Monheim (DE)

(72) Inventors: Thomas Seitz, Langenfeld (DE); Ulrike Wachendorff-Neumann, Neuwied (DE); Jürgen Benting, Leichlingen (DE); Peter Dahmen, Neuss (DE); Arnd Voerste, Köln (DE); Ralf Dunkel, Leichlingen (DE); Stefan Hillebrand, Neuss (DE); Klaus-Günther Tietjen, Langenfeld (DE); Stephane Brunet, Saint André de Corcy (FR)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/486,282

(22) Filed: Sep. 15, 2014

(65) Prior Publication Data

US 2015/0065551 A1    Mar. 5, 2015

Related U.S. Application Data

(62) Division of application No. 13/124,077, filed as application No. PCT/EP2009/007149 on Oct. 6, 2009, now Pat. No. 8,865,759.

(30) Foreign Application Priority Data

Oct. 15, 2008    (EP) .................................... 08166621

(51) Int. Cl.
*A01N 43/90* (2006.01)
*C07D 495/14* (2006.01)

(52) U.S. Cl.
CPC .............. *A01N 43/90* (2013.01); *C07D 495/14* (2013.01)

(58) Field of Classification Search
None
See application file for complete search history.

(56) References Cited

U.S. PATENT DOCUMENTS

| | | | |
|---|---|---|---|
| 3,364,229 A | 1/1968 | Draber et al. | |
| 8,729,118 B2 * | 5/2014 | Seitz et al. .................... | 514/411 |
| 2003/0176428 A1 | 9/2003 | Schneidersmann et al. | |
| 2010/0120884 A1 | 5/2010 | Seitz et al. | |
| 2011/0064827 A1 | 3/2011 | Seitz et al. | |
| 2011/0118115 A1 | 5/2011 | Seitz et al. | |
| 2011/0257009 A1 | 10/2011 | Seitz et al. | |
| 2011/0280958 A1 | 11/2011 | Seitz et al. | |
| 2011/0294662 A1 | 12/2011 | Seitz et al. | |

FOREIGN PATENT DOCUMENTS

| | | |
|---|---|---|
| JP | 10-251265 A | 9/1998 |
| WO | WO 89/10396 A1 | 11/1989 |
| WO | WO 96/33270 A1 | 10/1996 |
| WO | WO 02/28186 A2 | 4/2002 |
| WO | WO 02/080675 A1 | 10/2002 |
| WO | WO 2007/024782 A2 | 3/2007 |
| WO | WO 2007/027777 A2 | 3/2007 |

OTHER PUBLICATIONS

Draber, W., "Synthese von 1.4-Dithiinen aus Derivaten des Maleinimids," *Chem. Ber.* 100:1559-1570, Wiley-VCH, Germany (1967).

Draber, W. and Wegler, R., "Natürliche Pflanzenwuchsstoffe—Phytohormone: 2. Gibberelline," in *Chemie der Pflanzenschutz- und Schädlingsbekämpfungsmittel*, vol. 2, Wegler, R., ed., pp. 401-412, Springer-Verlag, Germany (1970).

English language translation of Draber, W. and Wegler, R., "Natürliche Pflanzenwuchsstoffe—Phytohormone: 2. Gibberelline," in *Chemie der Pflanzenschutz-und Schädlingsbekämpfungsmittel*, vol. 2, Wegler, R., ed., pp. 401-412, Springer-Verlag, Germany (1970).

Gaina, C. and Gaina, V., "Polyethers and polythioethers containing 1,4-dithiin-2,3;5,6-tetrayl diimide," *Designed Monomers and Polymers* 8(4):347-363, VSP, Netherlands (2005).

Valla, A., et al., "Atypical Oxidation Reaction by Thionyl Chloride: Easy Two-Step Synthesis of $N$-Alkyl-1,4-dithiines," *Synthetic Communication* 36:3591-3597, Taylor & Francis Group, LLC, England (2006).

Zentz, F., et al., "Antifouling Activities of $N$-Substituted Imides: Antimicrobial Activities and Inhibition of *Mytilus edulis* Phenoloxidase," *Mar. Biotechnol.* 4:431-440, Springer-Verlag New York Inc., United States (2002).

Zentz, F., et al., "Syntheses, in vitro antibacterial and antifungal activities of a series of $N$-alkyl, 1,4-dithiines," *Il Farmaco* 60:944-947, Elsevier SAS, France (2005).

Zentz, F., et al., "Syntheses, in vitro antibacterial and cytotoxic activities of a series of 3-substituted succinimides," *Il Farmaco* 59:879-886, Elsevier SAS, France (2004).

Zentz, F., et al., "Synthesis and antimicrobial activities of $N$-substituted imides," *Il Farmaco* 57:421-426, Éditions scientifiques et médicales Elsevier SAS, France (2002).

English language Abstract of Japanese Patent Publication No. JP 10-251265 A, published Sep. 22, 1998, European Patent Office, espacenet database—Worldwide.

International Search Report for International Application No. PCT/EP2009/007149, European Patent Office, Rijswijk, Netherlands, mailed on Feb. 17, 2010.

Restriction Requirement mailed May 5, 2011, in U.S. Appl. No. 12/578,744, Seitz, T., et al., filed Oct. 14, 2009.

(Continued)

*Primary Examiner* — Kamal Saeed

(74) *Attorney, Agent, or Firm* — Sterne, Kessler, Goldstein & Fox PLLC

(57) ABSTRACT

The present invention relates to the use of novel and of known dithiine-tetracarboximides for controlling phytopathogenic fungi, and to methods of controlling phytopathogenic fungi in plant protection, and to plant protection compositions comprising these dithiine-tetracarboximides.

11 Claims, No Drawings

(56) References Cited

OTHER PUBLICATIONS

Office Action mailed Jun. 28, 2011, in U.S. Appl. No. 12/578,744, Seitz, T., et al., filed Oct. 14, 2009.

Office Action mailed Jan. 9, 2013, in U.S. Appl. No. 12/881,281, Seitz, T., et al., filed Sep. 14, 2010, U.S. Patent and Trademark Office, Alexandria, VA.

Notice of Allowance mailed Mar. 26, 2013, in U.S. Appl. No. 12/881,281, Seitz, T., et al., filed Sep. 14, 2010, U.S. Patent and Trademark Office, Alexandria, VA.

Office Action mailed Jan. 11, 2013, in U.S. Appl. No. 13/086,450, Seitz, T., et al., filed Apr. 14, 2011, U.S. Patent and Trademark Office, Alexandria, VA.

Office Action mailed Dec. 20, 2012, in U.S. Appl. No. 13/086,921, Seitz, T., et al., filed Apr. 14, 2011, U.S. Patent and Trademark Office, Alexandria, VA.

Notice of Allowance mailed Apr. 4, 2013, in U.S. Appl. No. 12/947,961, Seitz, T. et al., filed Nov. 17, 2010, U.S. Patent and Trademark Office, Alexandria, VA.

Office Action mailed Dec. 20, 2012, in U.S. Appl. No. 13/087,231, Seitz, T., et al., filed Apr. 14, 2011, U.S. Patent and Trademark Office, Alexandria, VA.

Office Action mailed Aug. 7, 2013, in U.S. Appl. No. 13/087,231, Seitz, T., et al., filed Apr. 14, 2011, U.S. Patent and Trademark Office, Alexandria, VA.

* cited by examiner

USE OF DITHIINE-TETRACARBOXIMIDES FOR CONTROLLING PHYTOPATHOGENIC FUNGI

The present invention relates to the use of novel and of known dithiine-tetracarboximides for controlling phytopathogenic fungi, and to methods of controlling phytopathogenic fungi in plant protection, and to plant protection compositions comprising these dithiine-tetracarboximides.

Dithiine-tetracarboximides per se are already known. It is also known that these dithiine-tetracarboximides can be used as anthelmintics against internal parasites of animals, in particular nematodes, and that they have insecticidal activity (cf. U.S. Pat. No. 3,364,229). Furthermore, it is known that certain dithiine-tetracarboximides are antibacterially active and have a certain effect against mycosis in humans (cf. II Farmaco, 2005, 60, 944-947). Moreover, it is known that dithiine-tetracarboximides can be employed as pigments in electrophotographic photoreceptors or as colorants in varnishes and polymers (cf. JP-A 10-251265, PL-B 143804).

Since the ecological and economical demands made on modern fungicides keep getting more and more stringent, for example as regards the spectrum of action, toxicity, selectivity, application rate, formation of residues and advantageous production, and since furthermore for example resistance problems may occur, there is a constant need to develop novel fungicides which meet the abovementioned demands better, at least in some areas.

It has now been found that dithiine-tetracarboximides of the general formula (I)

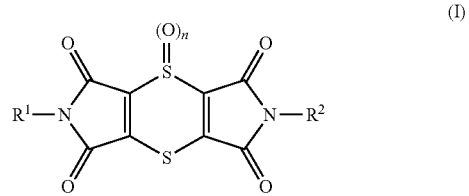

(I)

in which
$R^1$ and $R^2$ are identical or different and represent hydrogen, $C_1$-$C_8$-alkyl which is optionally monosubstituted or polysubstituted by halogen, —$OR^3$, —$COR^4$, or represent $C_3$-$C_7$-cycloalkyl which are optionally monosubstituted or polysubstituted by halogen, $C_1$-$C_4$-alkyl or $C_1$-$C_4$-haloalkyl, or represent aryl or aryl-($C_1$-$C_4$-alkyl), each of which is optionally monosubstituted or polysubstituted by halogen, $C_1$-$C_4$-alkyl, $C_1$-$C_4$-haloalkyl, —$COR^4$ or sulphonylamino,
$R^3$ represents hydrogen, $C_1$-$C_4$-alkyl, $C_1$-$C_4$-alkylcarbonyl, or represents aryl which is optionally monosubstituted or polysubstituted by halogen, $C_1$-$C_4$-alkyl or $C_1$-$C_4$-haloalkyl,
$R^4$ represents hydroxyl, $C_1$-$C_4$-alkyl or $C_1$-$C_4$-alkoxy,
n represents 0 or 1
are highly suitable for controlling phytopathogenic fungi.

Dithiine-tetracarboximides of the formula (I) according to the invention and, if appropriate, their salts are highly suitable for controlling phytopathogenic harmful fungi. The abovementioned compounds according to the invention show mainly a fungicidal activity and can be used not only in plant protection, in the domestic and hygiene fields, but also in the protection of materials.

Formula (I) provides a general definition of the dithiine-tetracarboximides which can be used in accordance with the invention. Carboximides of the formula (I) in which the radicals have the meanings hereinbelow can preferably be used.

$R^1$ and $R^2$ are preferably identical or different and preferably represent hydrogen, or represent $C_1$-$C_6$-alkyl which is optionally monosubstituted or polysubstituted by fluorine, chlorine, bromine, —$OR^3$, —$COR^4$, or represent $C_3$-$C_7$-cycloalkyl which is optionally monosubstituted or polysubstituted by chlorine, methyl or trifluoromethyl, or represent phenyl or phenyl-($C_1$-$C_4$-alkyl), each of which is optionally monosubstituted or polysubstituted by fluorine, chlorine, bromine, methyl, trifluoromethyl, —$COR^4$, sulphonylamino.

$R^1$ and $R^2$ are especially preferably identical or different and especially preferably represent hydrogen, or represent $C_1$-$C_4$-alkyl which is optionally monosubstituted or polysubstituted by fluorine, chlorine, hydroxyl, methoxy, ethoxy, methylcarbonyloxy, carboxyl, or represent $C_3$-$C_7$-cycloalkyl which is optionally monosubstituted or polysubstituted by chlorine, methyl or trifluoromethyl, or represent phenyl, benzyl, 1-phenethyl, 2-phenethyl or 2-methyl-2-phenethyl, each of which is optionally monosubstituted to trisubstituted by fluorine, chlorine, bromine, methyl, trifluoromethyl, —$COR^4$, sulphonylamino.

$R^1$ and $R^2$ are very especially preferably identical or different and very especially preferably represent hydrogen, methyl, ethyl, n-propyl, isopropyl, 2,2-difluoroethyl, 2,2,2-trifluoroethyl, or represent cyclopropyl or cyclohexyl, each of which is optionally substituted by chlorine, methyl or trifluoromethyl.

$R^1$ and $R^2$ particularly preferably simultaneously represent methyl.

$R^3$ preferably represents hydrogen, methyl, ethyl, methylcarbonyl, ethylcarbonyl or represents phenyl which is optionally monosubstituted or polysubstituted by fluorine, chlorine, methyl, ethyl, n-propyl, isopropyl or trifluoromethyl.

$R^3$ especially preferably represents hydrogen, methyl, methylcarbonyl or phenyl.

$R^4$ preferably represents hydroxyl, methyl, ethyl, methoxy or ethoxy.

$R^4$ especially preferably represents hydroxyl or methoxy.

n preferably represents 0.

n preferably also represents 1.

n especially preferably represents 0.

The following compounds may be mentioned individually:
(1) 2,6-Dimethyl-1H,5H-[1,4]dithiino[2,3-c:5,6-c']dipyrrole-1,3,5,7(2H,6H)-tetrone
(2) 2,6-Diethyl-1H,5H-[1,4]dithiino[2,3-c:5,6-c']dipyrrole-1,3,5,7(2H,6H)-tetrone
(3) 2,6-Dipropyl-1H,5H-[1,4]dithiino[2,3-c:5,6-c']dipyrrole-1,3,5,7(2H,6H)-tetrone
(4) 2,6-Di(propan-2-yl)-1H,5H-[1,4]dithiino[2,3-c:5,6-c']dipyrrole-1,3,5,7(2H,6H)-tetrone
(5) 2,6-Dicyclopropyl-1H,5H-[1,4]dithiino[2,3-c:5,6-c']dipyrrole-1,3,5,7(2H,6H)-tetrone
(6) 2,6-Bis(2,2,2-trifluoroethyl)-1H,5H-[1,4]dithiino[2,3-c:5,6-c']dipyrrole-1,3,5,7(2H,6H)-tetrone
(7) 2,6-Bis[1-(trifluoromethyl)cyclopropyl]-1H,5H-[1,4]dithiino[2,3-c:5,6-c']dipyrrole-1,3,5,7(2H,6H)-tetrone
(8) 1H,5H-[1,4]Dithiino[2,3-c:5,6-c']dipyrrole-1,3,5,7(2H,6H)-tetrone
(9) 2,6-Bis(3,5-dichlorophenyl)-1H,5H-[1,4]dithiino[2,3-c:5,6-c']dipyrrole-1,3,5,7(2H,6H)-tetrone
(10) 2,6-Diphenyl-1H,5H-[1,4]dithiino[2,3-c:5,6-c']dipyrrole-1,3,5,7(2H,6H)-tetrone
(11) 2,6-Dibenzyl-1H,5H-[1,4]dithiino[2,3-c:5,6-c']dipyrrole-1,3,5,7(2H,6H)-tetrone

(12) 2,6-Bis(2-methoxyethyl)-1H,5H-[1,4]dithiino[2,3-c:5,6-c']dipyrrole-1,3,5,7(2H,6H)-tetrone
(13) 2,6-Bis(2-hydroxybutyl)-1H,5H-[1,4]dithiino[2,3-c:5,6-c']dipyrrole-1,3,5,7(2H,6H)-tetrone
(14) 2,6-Bis(2-hydroxypropyl)-1H,5H-[1,4]dithiino[2,3-c:5,6-c']dipyrrole-1,3,5,7(2H,6H)-tetrone
(15) 2,6-Bis(2-phenoxyethyl)-1H,5H-[1,4]dithiino[2,3-c:5,6-c']dipyrrole-1,3,5,7(2H,6H)-tetrone
(16) 2,6-Bis(2-ethoxyethyl)-1H,5H-[1,4]dithiino[2,3-c:5,6-c']dipyrrole-1,3,5,7(2H,6H)-tetrone
(17) 2,6-Bis(2-phenylpropan-2-yl)-1H,5H-[1,4]dithiino[2,3-c:5,6-c']dipyrrole-1,3,5,7(2H,6H)-tetrone
(18) 2,6-Bis(1-phenylethyl)-1H,5H-[1,4]dithiino[2,3-c:5,6-c']dipyrrole-1,3,5,7(2H,6H)-tetrone
(19) 2,6-Bis(2-methoxy-2-methylpropyl)-1H,5H-[1,4]dithiino[2,3-c:5,6-c']dipyrrole-1,3,5,7(2H,6H)-tetrone
(20) 2,6-Di-tert-butyl-1H,5H-[1,4]dithiino[2,3-c:5,6-c']dipyrrole-1,3,5,7(2H,6H)-tetrone
(21) (1,3,5,7-Tetraoxo-1,3,5,7-tetrahydro-2H,6H-[1,4]dithiino[2,3-c:5,6-c']dipyrrole-2,6-diyl)diethane-2,1-diyl diacetate
(22) 4,4'-(1,3,5,7-Tetraoxo-1,3,5,7-tetrahydro-2H,6H-[1,4]dithiino[2,3-c:5,6-c']dipyrrole-2,6-diyl)dibenzenesulphonamide
(23) 2,2'-(1,3,5,7-Tetraoxo-1,3,5,7-tetrahydro-2H,6H-[1,4]dithiino[2,3-c:5,6-c']dipyrrole-2,6-diyl)diacetic acid
(24) 2,2'-(1,3,5,7-Tetraoxo-1,3,5,7-tetrahydro-2H,6H-[1,4]dithiino[2,3-c:5,6-c']dipyrrole-2,6-diyl)dipropanoic acid
(25) 2,2'-(1,3,5,7-Tetraoxo-1,3,5,7-tetrahydro-2H,6H-[1,4]dithiino[2,3-c:5,6-c']dipyrrole-2,6-diyl)dibutanoic acid
(26) 2,2'-(1,3,5,7-Tetraoxo-1,3,5,7-tetrahydro-2H,6H-[1,4]dithiino[2,3-c:5,6-c']dipyrrole-2,6-diyl)dihexanoic acid
(27) 2,2'-(1,3,5,7-Tetraoxo-1,3,5,7-tetrahydro-2H,6H-[1,4]dithiino[2,3-c:5,6-c]dipyrrole-2,6-diyl)bis(3,3-dimethylbutanoic acid)
(28) 3,3'-(1,3,5,7-Tetraoxo-1,3,5,7-tetrahydro-2H,6H-[1,4]dithiino[2,3-c:5,6-c']dipyrrole-2,6-diyl)dibutanoic acid
(29) 5,5'-(1,3,5,7-Tetraoxo-1,3,5,7-tetrahydro-2H,6H-[1,4]dithiino[2,3-c:5,6-c']dipyrrole-2,6-diyl)dipentanoic acid
(30) 2,6-Bis[3-(trifluoromethyl)cyclohexyl]-1H,5H-[1,4]dithiino[2,3-c:5,6-c']dipyrrole-1,3,5,7(2H,6H)-tetrone
(31) 2,6-Bis[3-(trifluoromethyl)phenyl]-1H,5H-[1,4]dithiino[2,3-c:5,6-c']dipyrrole-1,3,5,7(2H,6H)-tetrone
(32) 2,2'-(1,3,5,7-Tetraoxo-1,3,5,7-tetrahydro-2H,6H-[1,4]dithiino[2,3-c:5,6-c']dipyrrole-2,6-diyl)bis(3-phenylpropanoic acid)
(33) 2,6-Bis(2-hydroxyethyl)-1H,5H-[1,4]dithiino[2,3-c:5,6-c']dipyrrole-1,3,5,7(2H,6H)-tetrone
(34) 2,6-Bis(2-hydroxy-2-methylpropyl)-1H,5H-[1,4]dithiino[2,3-c:5,6-c']dipyrrole-1,3,5,7(2H,6H)-tetrone
(35) (1,3,5,7-Tetraoxo-1,3,5,7-tetrahydro-2H,6H-[1,4]dithiino[2,3-c:5,6-c']dipyrrole-2,6-diyl)dibutane-1,2-diyl diacetate
(36) (1,3,5,7-Tetraoxo-1,3,5,7-tetrahydro-2H,6H-[1,4]dithiino[2,3-c:5,6-c']dipyrrole-2,6-diyl)dipropane-1,2-diyl diacetate
(37) 2,6-Bis(hydroxymethyl)-1H,5H-[1,4]dithiino[2,3-c:5,6-c']dipyrrole-1,3,5,7(2H,6H)-tetrone
(38) 2,6-Dimethyl-1H,5H-[1,4]dithiino[2,3-c:5,6-c']dipyrrole-1,3,5,7(2H,6H)-tetrone 4-oxide
(39) 2-Ethyl-1H,5H-[1,4]dithiino[2,3-c:5,6-c']dipyrrole-1,3,5,7(2H,6H)-tetrone
(40) Diethyl 2,2'-(1,3,5,7-tetraoxo-1,3,5,7-tetrahydro-2H,6H-[1,4]dithiino[2,3-c:5,6-c']dipyrrole-2,6-diyl)-dihexanoate
(41) 2-[2-(1-Ethoxy-1-oxobutan-2-yl)-1,3,5,7-tetraoxo-2,3,5,7-tetrahydro-1H,6H-[1,4]dithiino[2,3-c:5,6-c']-dipyrrole-6-yl]butanoic acid.

Compounds (1), (2) and (3) can be used with special preference.

Novel dithiine-tetracarboximides are those of the formula (I-a)

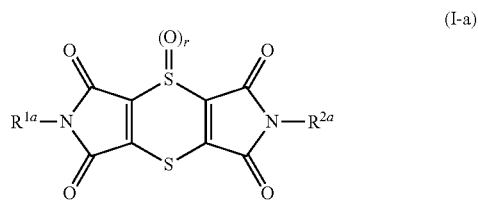

in which
$R^{1a}$ and $R^{2a}$ are identical or different and represent $C_1$-$C_8$-alkyl which is monosubstituted or polysubstituted by fluorine, —$OR^{3a}$, —$COR^{4a}$, or represent $C_3$-$C_7$-cycloalkyl which is optionally monosubstituted or polysubstituted by halogen, $C_1$-$C_4$-alkyl or $C_1$-$C_4$-haloalkyl, or represent aryl-($C_1$-$C_4$-alkyl) which is monosubstituted in the alkyl moiety by —$COR^{4a}$,
$R^{3a}$ represents $C_1$-$C_4$-alkyl, $C_1$-$C_4$-alkylcarbonyl, or represents aryl which is optionally monosubstituted or polysubstituted by halogen, $C_1$-$C_4$-alkyl or $C_1$-$C_4$-haloalkyl,
$R^{4a}$ represents hydroxyl, $C_1$-$C_4$-alkyl or $C_1$-$C_4$-alkoxy,
r represents 0 or 1,
where $R^{1a}$ and $R^{2a}$ do not simultaneously represent acetoxymethyl or methoxymethyl.

$R^{1a}$ and $R^{2a}$ are preferably identical or different and preferably represent $C_1$-$C_6$-alkyl which is monosubstituted or polysubstituted by fluorine, —$OR^{3a}$, —$COR^{4a}$, or represent $C_3$-$C_7$-cycloalkyl which is optionally monosubstituted or polysubstituted by chlorine, methyl or trifluoromethyl, or represent phenyl-($C_1$-$C_4$-alkyl) which is monosubstituted in the alkyl moiety by —$COR^{4a}$.

$R^{1a}$ and $R^{2a}$ are especially preferably identical or different and especially preferably represent $C_1$-$C_4$-alkyl which is monosubstituted or polysubstituted by fluorine, hydroxyl, methoxy, ethoxy, methylcarbonyloxy, carboxyl, or represent $C_3$-$C_7$-cycloalkyl which is optionally monosubstituted or polysubstituted by chlorine, methyl or trifluoromethyl, or represent 1-phenethyl or 2-phenethyl, each of which is monosubstituted in the alkyl moiety by —$COR^{4a}$.

$R^{1a}$ and $R^{2a}$ are very especially preferably identical or different and very especially preferably represent 2,2-difluoroethyl, 2,2,2-trifluoroethyl, or represent cyclopropyl or cyclohexyl, each of which is optionally substituted by chlorine, methyl or trifluoromethyl.

$R^{3a}$ preferably represents methyl, ethyl, methylcarbonyl, ethylcarbonyl, or represents phenyl which is optionally monosubstituted or polysubstituted by fluorine, chlorine, methyl, ethyl, n-propyl, isopropyl or trifluoromethyl.

$R^{3a}$ especially preferably represents methyl, methylcarbonyl or phenyl.

$R^{4a}$ preferably represents hydroxyl, methyl, ethyl, methoxy or ethoxy.

$R^{4a}$ especially preferably represents hydroxyl or methoxy.
r preferably represents 0.
r preferably also represents 1.
r especially preferably represents 0.

Depending on the nature of the above-defined substituents, the compounds of the formula (I) can have acidic or basic properties and can form salts, if appropriate also internal salts, or adducts with inorganic or organic acids or with bases or with metal ions.

Suitable metal ions are, in particular, the ions of the elements of the second main group, in particular calcium and magnesium, of the third and fourth main group, in particular aluminium, tin and lead, and of the first to eighth subgroup, in particular chromium, manganese, iron, cobalt, nickel, copper, zinc and others. Especially preferred are the metal ions of the elements of the fourth period. In this context, the metals can be present in the various valencies which they can assume.

If the compounds of the formula (I) have attached to them hydroxyl, carboxyl or other groups which induce acidic properties, these compounds can be reacted with bases to give salts.

Examples of suitable bases are hydroxides, carbonates, hydrogencarbonates of the alkali and alkaline earth metals, in particular those of sodium, potassium, magnesium and calcium, furthermore ammonia, primary, secondary and tertiary amines with $(C_1-C_4-)$-alkyl radicals, mono-, di- and trialkanolamines of $(C_1-C_4)$-alkanols, choline and chlorocholine.

If the compounds of the formula (I) have amino, alkylamino or other groups which induce basic properties attached to them, then these compounds can be reacted with acids to give salts.

Examples of inorganic acids are hydrohalic acids such as hydrofluoric acid, hydrochloric acid, hydrobromic acid and hydriodic acid, sulphuric acid, phosphoric acid and nitric acid, and acidic salts such as $NaHSO_4$ and $KHSO_4$.

Organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids with straight-chain or branched alkyl radicals having 1 to 20 carbon atoms), arylsulphonic acids or -disulphonic acids (aromatic radicals, such as phenyl and naphthyl, which have one or two sulphonyl groups attached to them), alkylphosphonic acids (phosphonic acids with straight-chain or branched alkyl radicals having 1 to 20 carbon atoms), arylphosphonic acids or aryldiphosphonic acids (aromatic radicals, such as phenyl and naphthyl, which have one or two phosphonic acid radicals attached to them), it being possible for the alkyl or aryl radicals to have attached to them further substituents, for example p-toluenesulphonic acid, salicylic acid, p-aminosalicylic acid, 2-phenoxybenzoic acid, 2-acetoxybenzoic acid etc.

The salts which can thus be obtained also have fungicidal properties.

The dithiine-tetracarboximides of the formula (I) which can be used in accordance with the invention can be prepared in a known manner (cf. U.S. Pat. No. 3,364,229, Synthetic Commun. 2006, 36, 3591-3597 and 11 Farmaco 2005, 60, 944-947).

In a first process, for example (cf. II Farmaco 2005, 60, 944-947), succinic anhydride of the formula (II) is reacted, in a first step, with an amine of the formula (III), if appropriate in the presence of a diluent. Thereafter, the resulting succinic monoamides of the formula (IV) are then reacted with a sulphur source (for example thionyl chloride). Depending on the reaction conditions, the dithiine-diisoimides of the formula (V) can be isolated before they are converted into the dithiine-tetracarboximides of the formula (I-b). The preparation of the dithiine-tetracarboximides of the formula (I) can be illustrated by the following scheme (in which R is $R^1$ or $R^2$):

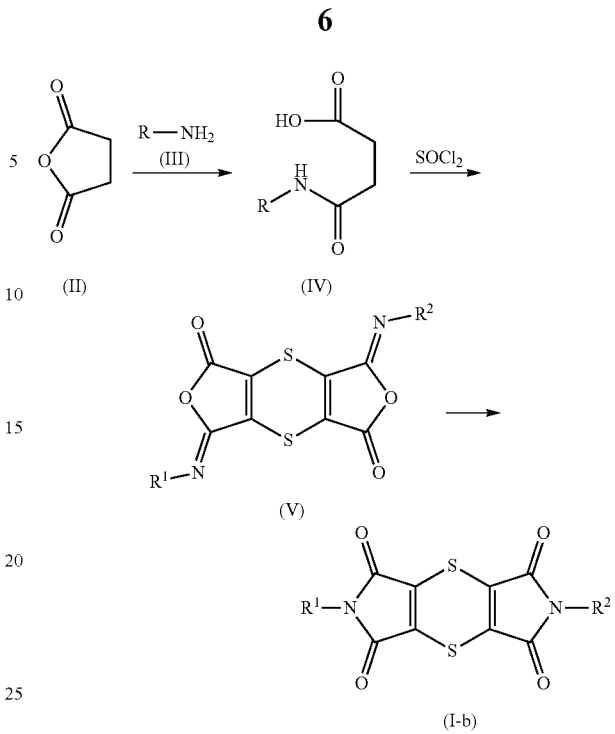

The dithiine-diisoimides of the formula (V)

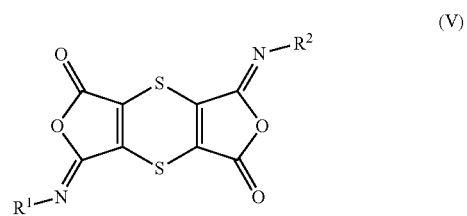

in which $R^1$ and $R^2$ have the abovementioned meanings are also suitable for controlling phytopathogenic fungi.

Here, $R^1$ and $R^2$ have the abovementioned preferred, especially preferred, very especially preferred or particularly preferred meanings.

Novel dithiine-diisoimides are those of the formula (V-a)

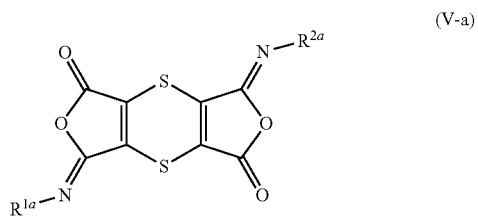

in which $R^{1a}$ and $R^{2a}$ have the abovementioned meanings.

$R^{1a}$ and $R^{2a}$ have the abovementioned preferred, especially preferred, very especially preferred or particularly preferred meanings.

In a second process, for example (cf. U.S. Pat. No. 3,364,229, Synthetic Commun. 2006, 36, 3591-3597), dichloromaleic anhydride, of the formula (VI), is reacted, in a first step, with an amine of the formula (III), if appropriate in the presence of a diluent. Thereafter, the resulting maleic imides of the formula (VII) are then reacted with a sulphur source (for example hydrogen disulphide or thiourea). If appropriate, the resulting dithiine-tetracarboximides of the formula (I-b) can subsequently be oxidized with nitric acid. The preparation of the dithiine-tetracarboximides of the formula (I) can be illustrated by the following scheme (in which R is $R^1$ or $R^2$):

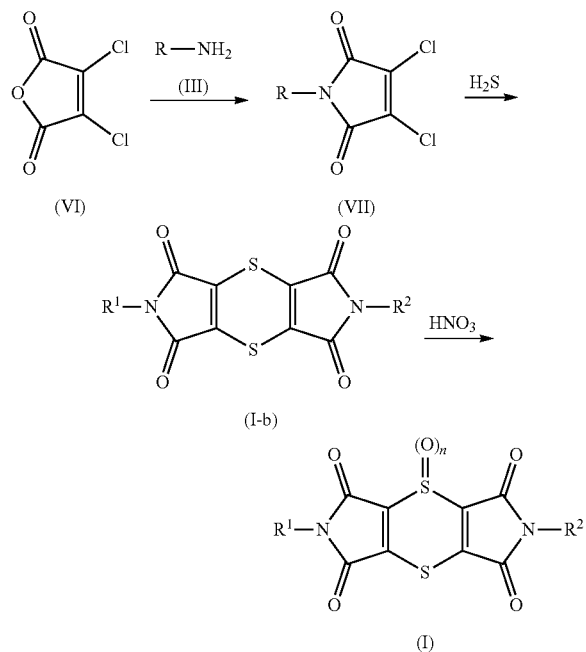

The present invention furthermore relates to a plant protection composition for controlling undesired fungi, comprising at least one dithiine-tetracarboximide of the formula (I) or a dithiine-diisoimide of the formula (V). These preferably take the form of fungicidal compositions which comprise agriculturally useable adjuvants, solvents, carriers, surface-active substances or extenders.

Furthermore, the invention relates to a method of controlling undesired microorganisms, characterized in that dithiine-tetracarboximides of the formula (I) or dithiine-diisoimides of the formula (V) are applied in accordance with the invention to the phytopathogenic fungi and/or their environment.

According to the invention, carrier is to be understood as meaning a natural or synthetic, organic or inorganic substance which is mixed or combined with the active substances for better applicability, in particular for application to plants or plant parts or seeds. The carrier, which may be solid or liquid, is generally inert and should be suitable for use in agriculture.

Suitable solid or liquid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilisers, water, alcohols, especially butanol, organic solvents, mineral and vegetable oils and derivatives of these. Mixtures of such carriers may also be used. Suitable carriers for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers are liquids which are gaseous at ambient temperature and under atmospheric pressure, for example aerosol propellants, such as halocarbons, and also butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible, for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surface-active substances. Suitable surface-active substances are emulsifiers and/or foam formers, dispersants or wetting agents having ionic or nonionic properties, or mixtures of these surface-active substances. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example, alkylaryl polyglycol ethers, alkylsulphonates, alkyl sulphates, arylsulphonates, protein hydrolysates, lignin-sulphite waste liquors and methylcellulose. The presence of a surface-active substance is required if one of the active substances and/or one of the inert carriers is insoluble in water and when the application takes place in water. The proportion of surface-active substances is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestring agents, complex formers. In general, the active substances can be combined with any solid or liquid additive customarily used for formulation purposes.

In general, the formulations contain between 0.05 and 99% by weight, 0.01 and 98% by weight, preferably between 0.1 and 95% by weight, especially preferably between 0.5 and 90% by weight of active substance, very especially preferably between 10 and 70 percent by weight.

The active substances or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active substance, and also microencapsulations in polymeric substances and in coating materials for seed, and also ULV cold-fogging and warm-fogging formulations.

The formulations mentioned can be prepared in a manner known per se, for example by mixing the active substances with at least one customary extender, solvent or diluent, emulsifier, dispersant and/or binder or fixing agent, wetting agent, water repellant, if appropriate siccatives and UV stabilizers and, if appropriate, dyes and pigments, defoamers, preservatives, secondary thickeners, adhesives, gibberellins and also further processing auxiliaries.

The compositions according to the invention do not only comprise ready-to-use compositions which can be applied with suitable apparatus to the plant or the seed, but also commercial concentrates which have to be diluted with water prior to use.

The active substances according to the invention, per se or in their (commercially available) formulations and in the use forms prepared from these formulations, may be present in a mixture with other (known) active substances such as insecticides, attractants, sterilants, bactericides, acaricides, nematicides, fungicides, growth regulators, herbicides, fertilisers, safeners or semiochemicals.

The treatment according to the invention of the plants and plant parts with the active substances or compositions is carried out directly or by action on their surroundings, habitat or storage space using customary treatment methods, for example by dipping, spraying, atomizing, irrigating, evaporating, dusting, fogging, broadcasting, foaming, painting, spreading-on, drenching, drip irrigating and, in the case of propagation material, in particular in the case of seeds, furthermore by dry seed treatment, by wet seed treatment, by slurry treatment, by incrusting, by coating with one or more coats, etc. It is furthermore possible to apply the active substances by the ultra-low-volume method, or to inject the active substance preparation, or the active substance itself, into the soil.

The invention furthermore comprises a method for the treatment of seed.

The invention furthermore relates to seed which has been treated in accordance with one of the methods described in the previous paragraph. The seeds according to the invention are used in methods for the protection of seed from undesirable fungi. Here, a seed treated with at least one active substance according to the invention is used.

The active substances or compositions according to the invention are also suitable for treating seed. A large part of the damage to crop plants caused by harmful organisms is triggered by the infection of the seed during storage or after sowing as well as during and after germination of the plant. This phase is particularly critical since the roots and shoots of the growing plant are particularly sensitive, and even just small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of plant protection compositions after sowing or after the emergence of the plants or which at least considerably reduce additional application. It is furthermore desirable to optimize the amount of active substance employed in such a way as to provide maximum protection for the seed and the germinating plant from attack by phytopathogenic fungi, but without damaging the plant itself by the active substance employed. In particular, methods for the treatment of seed should also take into consideration the intrinsic fungicidal properties of transgenic plants in order to achieve optimum protection of the seed and the germinating plant with a minimum of plant protection compositions being employed.

Accordingly, the present invention also relates to a method for protecting seed and germinating plants against attack by phytopathogenic fungi by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with plant protection compositions. Owing to the concerns regarding a possible impact of the plant protection compositions on the environment and the health of humans and animals, there are efforts to reduce the amount of active substances applied.

One of the advantages of the present invention is that, because of the particular systemic properties of the active substances or compositions according to the invention, treatment of the seed with these active substances or compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the active substances or compositions according to the invention can be used in particular also for transgenic seed where the plant growing from this seed is capable of expressing a protein which acts against pests. By treating such seed with the active substances or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture, in the greenhouse, in forests or in horticulture and viticulture. In particular, this takes the form of seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cacao, sugar cane, tobacco, vegetables (such as tomato, cucumbers, onions and lettuce), turf and ornamentals (see also hereinbelow). Of particular importance is the treatment of the seed of cereals (such as wheat, barley, rye, triticale and oats), maize and rice.

As also described hereinbelow, the treatment of transgenic seed with the active substances or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

In the context of the present invention, the composition according to the invention is applied on its own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active substances which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active substances which can be used according to the invention can be converted into the customary seed-dressing product formulations such as solutions, emulsions, suspensions, powders, foams, slurries and other coating compositions for seed, and ULV formulations.

These formulations are prepared in the known manner by mixing the active substances with customary additives such as, for example, customary extenders and also solvents or diluents, colorants, wetters, dispersants, emulsifiers, antifoams, preservatives, secondary thickeners, adhesives, gibberellins, and also water.

Colorants which may be present in the seed-dressing product formulations which can be used according to the invention are all colorants which are customary for such purposes. Both pigments, which are sparingly soluble in water, and dyes, which are soluble in water, may be used. Examples of colorants which may be mentioned are those known by the names Rhodamin B, C.I. Pigment Red 112 and C.I. Solvent Red 1.

Wetters which may be present in the seed-dressing product formulations which can be used according to the invention are all substances which are conventionally used for the formulation of agrochemical active substances and for promoting wetting. Alkylnaphthalenesulphonates, such as diisopropyl- or diisobutylnaphthalenesulphonates, can preferably be used.

Suitable dispersants and/or emulsifiers which may be present in the seed-dressing product formulations which can be used in accordance with the invention are all non-ionic, anionic and cationic dispersants which are conventionally used for the formulation of agrochemical active substances. Non-ionic or anionic dispersants or mixtures of non-ionic or anionic dispersants can preferably be used. Suitable non-ionic dispersants which may be mentioned are, in particular, ethylene oxide/propylene oxide block polymers, alkylphenol polyglycol ethers and tristyrylphenol polyglycol ethers, and their phosphated or sulphated derivatives. Suitable anionic dispersants are, in particular, lignosulphonates, polyacrylic acid salts and arylsulphonate/formaldehyde condensates.

Antifoams which may be present in the seed-dressing product formulations which can be used according to the invention are all foam-suppressing substances conventionally used for the formulation of agrochemical active substances. Silicone antifoams and magnesium stearate can preferably be used.

Preservatives which may be present in the seed-dressing product formulations which can be used according to the invention are all substances which can be employed in agrochemical compositions for such purposes. Examples which may be mentioned are dichlorophene and benzyl alcohol hemiformal.

Secondary thickeners which may be present in the seed-dressing product formulations which can be used according to the invention are all substances which can be employed in agrochemical compositions for such purposes. Cellulose derivatives, acrylic acid derivatives, xanthan, modified clays and highly disperse silica are preferably suitable.

Adhesives which may be present in the seed-dressing product formulations which can be used according to the invention are all customary binders which can be employed in seed-dressing products. Polyvinylpyrrolidone, polyvinyl acetate, polyvinyl alcohol and tylose may be mentioned by preference.

Gibberellins which may be present in the seed-dressing product formulations which can be used according to the invention are preferably the gibberellins A1, A3 (=gibberellic acid), A4 and A7, with gibberellic acid being particularly preferably used. The gibberellins are known (cf. R. Wegler "Chemie der Pflanzenschutz-und Schädlingsbekämpfungsmittel" [Chemistry of Plant Protectants and Pesticides], Vol. 2, Springer Verlag, 1970, pp. 401-412).

The seed-dressing product formulations which can be used in accordance with the invention can be employed either directly or after previous dilution with water for the treatment of a wide range of seeds, including the seed of transgenic plants. In this context, additional synergistic effects may also occur as a consequence of the interaction with the substances formed by expression.

Suitable apparatuses which can be employed for treating seed with the seed-dressing product formulations which can be used in accordance with the invention, or with the preparations prepared therefrom by addition of water, are all mixing apparatuses which can usually be employed for dressing seed. Specifically, a seed-dressing procedure is followed in which the seed is placed in a mixer, the amount of seed-dressing product formulation desired in each case is added, either as such or after previously diluting it with water, and the contents of the mixer are mixed until the formulation has been distributed uniformly on the seed. If appropriate, this is followed by a drying process.

The active substances or compositions according to the invention have a potent fungicidal activity and can be employed for controlling undesired fungi in plant protection and in the protection of materials.

The dithiine-tetracarboximides according to the invention can be applied in plant protection for controlling plasmodiophoromycetes, oomycetes, chytridiomycetes, zygomycetes, ascomycetes, basidiomycetes and deuteromycetes.

The fungicidal compositions according to the invention can be employed curatively or protectively for controlling phytopathogenic fungi. The invention therefore also relates to curative and protective methods of controlling phytopathogenic fungi by using the active substances or compositions according to the invention, which are applied to the seed, the plant or plant parts, the fruits or the soil in which the plants grow.

The compositions according to the invention for controlling phytopathogenic fungi in plant protection comprise an effective, but nonphytotoxic amount of the active substances according to the invention. "Effective, but nonphytotoxic amount" means such an amount of the composition according to the invention which suffices for sufficiently controlling or fully eradicating the fungal disease of the plant while simultaneously not entailing substantial phytotoxicity symptoms. In general, this application rate can vary within a substantial range. It depends on a plurality of factors, for example on the fungus to be controlled, the plant, the climatic conditions and the constituents of the compositions according to the invention.

The good plant tolerance of the active substances at the concentrations required for controlling plant diseases permits the treatment of aerial plant parts, of rigiditive propagation material and of seed, and of the soil.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

The active substances according to the invention are suitable for the protection of plants and plant organs, for increasing the yields, for improving the quality of the harvested crop, while being well tolerated by plants, having favourable toxicity to warm-blooded species and being environmentally friendly. They can preferably be employed as plant protection compositions. They are active against normally sensitive and resistant species and against all or individual developmental stages.

Plants which can be treated in accordance with the invention and which may be mentioned are the following: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana plants and banana plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumbers), Alliaceae sp. (for example leeks, onions), Papilionaceae sp. (for example peas); major crop plants such as Gramineae sp. (for example maize, turf, cereals such as wheat, rye, rice, barley, oats, sorghum, millet and triticale), Asteraceae sp. (for example sunflower), Brassicaceae sp. (for example white cabbage, red cabbage, broccoli, cauliflower, Brussels sprouts, pak choi, kohlrabi, small radishes, and also oilseed rape, mustard, horseradish and cress), Fabacae sp. (for example beans, peanuts), Papilionaceae sp. (for example soya beans), Solanaceae sp. (for example potatoes), Chenopodiaceae sp. (for example sugar beet, fodder beet, swiss chard, beetroot); useful plants and ornamentals in gardens and forests; and in each case genetically modified types of these plants.

As has already been mentioned above, all plants and their parts may be treated in accordance with the invention. In a preferred embodiment, plant species and plant varieties, and their parts, which grow wild or which are obtained by traditional biological breeding methods such as hybridization or protoplast fusion are treated. In a further preferred embodiment, transgenic plants and plant varieties which have been obtained by recombinant methods, if appropriate in combination with traditional methods (genetically modified organisms), and their parts are treated. The term "parts" or "parts of plants" or "plant parts" has been explained hereinabove. Plants of the plant varieties which are in each case commercially available or in use are especially preferably treated in accordance with the invention. Plant varieties are understood as meaning plants with novel traits which have been bred both by traditional breeding, by mutagenesis or by recombinant DNA techniques. They may take the form of varieties, races, biotypes and genotypes.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active substances and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active substance combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defence system of plants in such a way that, when subsequently inoculated with unwanted phytopathogenic fungi, the treated plants display a substantial degree of resistance to these unwanted phytopathogenic fungi. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active substances.

Plants and plant varieties which are preferably to be treated according to the invention include all plants which have genetic material which imparts particularly advantageous, useful traits to these plants (whether obtained by breeding and/or biotechnological means).

Plants and plant varieties which are also preferably to be treated according to the invention are resistant against one or more biotic stresses, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stresses. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a *petunia* EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase are described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenyl pyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme of prephenate dehydrogenase in addition to a gene encoding an HPPD-tolerant enzyme.

Still further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio) benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, selection in cell cultures in the presence of the herbicide or mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed online at: http/www.lifesci.sussex-.ac.uk/Home/Neil_Crickmore/Bt/, or insecticidal portions thereof, e.g. proteins of the Cry protein classes Cry1Ab, Cry1Ac, Cry1F, Cry2Ab, Cry3Ae, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb1 protein in corn events MON863 or MON88017, or the Cry3A protein in corn event MIR 604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g. proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose)polymerase (PARP) gene in the plant cells or plants.

b. plants which contain a stress tolerance-enhancing transgene capable of reducing the expression and/or the activity of the PARG-encoding genes of the plants or plant cells.

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the crop product and/or altered properties of specific ingredients of the crop product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications.

2) transgenic plants which synthesize non-starch carbohydrate polymers or which synthesize non-starch carbohydrate polymers with altered properties in comparison to wild type plants without genetic modification. Examples are plants which produce polyfructose, especially of the inulin and levan type, plants which produce alpha-1,4-glucans, plants which produce alpha-1,6 branched alpha-1,4-glucans, and plants producing alternan.

3) transgenic plants which produce hyaluronan.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants which contain an altered form of cellulose synthase genes, b) plants, such as cotton plants which contain an altered form of rsw2 or rsw3 homologous nucleic acids;

c) plants, such as cotton plants, with an increased expression of sucrose phosphate synthase;

d) plants, such as cotton plants, with an increased expression of sucrose synthase;

e) plants, such as cotton plants, wherein the timing of the plasmodesmatal gating at the basis of the fibre cell is altered, e.g. through downregulation of fibre-selective β-1,3-glucanase;

f) plants, such as cotton plants, which have fibres with altered reactivity, e.g. through the expression of the N-acetylglucosaminetransferase gene including nodC and chitin synthase genes.

Plants or plant varieties (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Particularly useful transgenic plants which may be treated according to the invention are plants which comprise one or more genes which encode one or more toxins are the following which are sold under the trade names YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

The active substances or compositions according to the invention may furthermore be employed in the protection of materials for protecting industrial materials against attack and destruction by undesired microorganisms such as, for example, fungi.

In the present context, industrial materials are understood as meaning nonlive materials which have been prepared for use in industry. Industrial materials which are intended to be protected by active substances according to the invention from change or destruction by fungi can be, for example, glues, sizes, paper, wall card and board, textiles, carpets, leather, wood, paints and plastic articles, cooling lubricants and other materials which are capable of being attacked or decomposed by microorganisms. Other materials to be protected and which can be adversely affected by the multiplication of microorganisms which may be mentioned within the scope are parts of production plants and buildings, for example cooling water circuits, cooling and heating systems and aeration and air-conditioning units. Industrial materials which may be mentioned by preference within the scope of the present invention are glues, sizes, paper and boards, leather, wood, paints, cooling lubricants and heat-transfer fluids, especially preferably wood. The active substances or compositions according to the invention can prevent disadvantageous effects such as wilting, decay, discolouration, decolouration or mould development. Moreover, the compounds according to the invention can be employed for protecting objects against being covered with growth, in particular ships' hulls, sieves, nets, buildings, jetties and signal units, which come into contact with seawater or brackish water.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected in the freshly harvested state or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, pelts, leather, furs and hairs. The active substances according to the invention can prevent disadvantageous effects, such as rotting, decay, discolouration, decolouration or the development of mould.

Some pathogens of fungal diseases which can be treated according to the invention may be mentioned, by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

Diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example, *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

Leaf blotch diseases and leaf wilt diseases caused, for example, by *Alternaria* species, such as, for example, *Alternaria solani*; *Cercospora* species, such as, for example, *Cercospora beticola*; *Cladiosporum* species, such as, for example, *Cladiosporium cucumerinum*; *Cochliobolus* species, such as, for example, *Cochliobolus sativus* (conidia form: *Drechslera*, Syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*, *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola* and *M. fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia collo-cygni*; *Rhynchosporium* species, such as, for example, *Rhynchosporium secalis*; *Septoria* species, such as, for example, *Septoria apii*; *Typhula* species, such as, for example, *Typhula incarnata*; *Venturia* species, such as, for example, *Venturia inaequalis*;

Root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Rhizoctonia* species, such as, for example, *Rhizoctonia solani*; *Tapesia* species, such as, for example, *Tapesia acuformis*; *Thielaviopsis* species, such as, for example, *Thielaviopsis basicola*;

Ear and panicle diseases (including maize cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Septoria* species, such as, for example, *Septoria nodorum*;

Diseases caused by smut fungi, such as, for example, *Sphacelotheca* species, such as, for example, *Sphacelotheca reiliana*; *Tilletia* species, such as, for example, *Tilletia caries*, *T. controversa*; *Urocystis* species, such as, for example, *Urocystis occulta*; *Ustilago* species, such as, for example, *Ustilago nuda*, *U. nuda tritici*;

Fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* and *P. purpurogenum*; *Sclerotinia* species, such as, for example, *Sclerotinia sclerotiorum*; *Verticilium* species, such as, for example, *Verticilium alboatrum*;

Seed- and soil-borne rot and wilt diseases, and also diseases of seedlings, caused, for example, by *Fusarium* species, such as, for example, *Fusarium culmorum*; *Phytophthora* species, such as, for example, *Phytophthora cactorum*; *Pythium* species, such as, for example, *Pythium ultimum*; *Rhizoctonia* species, such as, for example, *Rhizoctonia solani*; *Sclerotium* species, such as, for example, *Sclerotium rolfsii*;

Cancerous diseases, galls and witches' broom caused, for example, by *Nectria* species, such as, for example, *Nectria galligena*;

Wilt diseases caused, for example, by *Monilinia* species, such as, for example, *Monilinia laxa*;

Deformations of leaves, flowers and fruits caused, for example, by *Taphrina* species, such as, for example, *Taphrina deformans*;

Degenerative diseases of woody plants caused, for example, by *Esca* species, such as, for example, *Phaemoniella clamydospora* and *Phaeoacremonium aleophilum* and *Fomitiporia mediterranea*;

Diseases of flowers and seeds caused, for example, by *Botrytis* species, such as, for example, *Botrytis cinerea*;

Diseases of plant tubers caused, for example, by *Rhizoctonia* species, such as, for example, *Rhizoctonia solani*; *Helminthosporium* species, such as, for example, *Helminthosporium solani*;

Diseases caused by bacteriopathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*.

Preference is given to controlling the following diseases of soya beans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (dactuliophora glycines), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*, *Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum*, *Fusarium orthoceras*, *Fusarium semitectum*, *Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum*, *Pythium irregulare*, *Pythium debaryanum*, *Pythium myriotylum*, *Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

Organisms which can bring about degradation or modification of the industrial materials and which may be mentioned are fungi. The active substances according to the invention are preferably active against fungi, in particular moulds, wood-discolouring and wood-destroying fungi (Basidiomycetes). Fungi of the following genera may be mentioned by way of example: *Alternaria*, such as *Alternaria* tenuis; *Aspergillus*, such as *Aspergillus niger*, *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*, *Aureobasidium*, such as *Aureobasidium pullulans*; *Sclerophoma*, such as *Sclerophoma pityophila*; *Trichoderma*, such as *Trichoderma viride*.

Moreover, the active substances according to the invention also have very good antimycotic activities. They have a very broad antimycotic spectrum of action, in particular against dermatophytes and spreading fungi, mould and diphasic fungi (for example against *Candida* species such as *Candida albicans*, *Candida glabrata*) and against *Epidermophyton floccosum*, *Aspergillus* species such as *Aspergillus niger* and *Aspergillus fumigatus*, *Trichophyton* species such as *Trichophyton mentagrophytes*, *Microsporon* species such as *Microsporon canis* and *audouinii*. The enumeration of these fungi on no account constitutes a limitation of the mycotic spectrum which can be controlled, but only has illustrative character.

When employing the active substances according to the invention as fungicides, the application rates may vary within a substantial range, depending on the type of application. The application rate of the active substances according to the invention is when treating plant parts, for example leaves: from 0.1 to 10 000 g/ha, preferably from 10 to 1000 g/ha, particularly preferably from 50 to 300 g/ha (when the application is carried out by watering or dropwise, it may even be possible to reduce the application rate, in particular when inert substrates such as rock wool or perlite are used);

when treating seed: from 2 to 200 g per 100 kg of seed, preferably from 3 to 150 g per 100 kg of seed, especially preferably from 2.5 to 25 g per 100 kg of seed, very especially preferably from 2.5 to 12.5 g per 100 kg of seed;

when treating the soil: from 0.1 to 10 000 g/ha, preferably from 1 to 5000 g/ha.

These application rates are mentioned only by way of example and not by way of limitation in the sense of the invention.

The active substances or compositions according to the invention can thus be employed for protecting plants for a certain period of time after treatment against attack by the pathogens mentioned. The period for which protection is provided extends generally for 1 to 28 days, preferably 1 to 14 days, particularly preferably 1 to 10 days, very particularly preferably 1 to 7 days after the treatment of the plants with the active substances, or up to 200 days after the treatment of seed.

In addition, by the treatment according to the invention it is possible to reduce the mycotoxin content in the harvested material and the foodstuff and feedstuff prepared therefrom. Particular, but not exclusive, mention may be made here of the following mycotoxins: deoxynivalenol (DON), nivalenol, 15-Ac-DON, 3-Ac-DON, T2- and HT2-toxin, fumonisine, zearalenon, moniliformin, fusarin, diaceotoxyscirpenol (DAS), beauvericin, enniatin, fusaroproliferin, fusarenol, ochratoxins, patulin, ergot alkaloids and aflatoxins produced, for example, by the following fungi: *Fusarium* spec., such as *Fusarium acuminatum*, *F. avenaceum*, *F. crookwellense*, *F. culmorum*, *F. graminearum* (*Gibberella zeae*), *F. equiseti*, *F. fujikoroi*, *F. musarum*, *F. oxysporum*, *F. proliferatum*, *F. poae*, *F. pseudograminearum*, *F. sambucinum*, *F. scirpi*, *F. semitectum*, *F. solani*, *F. sporotrichoides*, *F. langsethiae*, *F. subglutinans*, *F. tricinctum*, *F. verticillioides*, inter alia, and also by *Aspergillus* spec., *Penicillium* spec., *Claviceps purpurea*, *Stachybotrys* spec. inter alia.

The abovementioned plants can be treated especially advantageously in accordance with the invention with the compounds of the general formula (I) or with dithiine-diisoimides of the formula (V) or with the compositions according to the invention. The preferred ranges indicated above for the active substances or compositions also apply to the treatment of these plants. The treatment of plants with the compounds or compositions mentioned specifically in the present text should be especially emphasised.

PREPARATION EXAMPLES

Preparation of 2,6-bis[1-(trifluoromethyl)cyclopropyl]-1H,5H-[1,4]dithiino[2,3-c:5,6-c']dipyrrole-1,3, 5,7-(2H,6H)-tetrone [compound No. (7)]

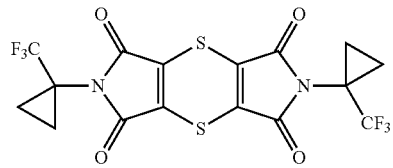 [SMILES: O=c1c2sc3c(=O)n(C4(C(F)(F)F)CC4)c(=O)c3sc2c(=O)n1C1(C(F)(F)F)CC1]

Slowly, 7.57 ml (103.75 mmol) of thionyl chloride were added dropwise to a solution of 0.8 g (3.55 mmol) of 4-oxo-4-{[1-(trifluoromethyl)cyclopropyl]amino}butanoic acid (IV-1) in 2 ml of dioxane, with ice-cooling (15° C.). The mixture was allowed to warm to room temperature overnight, and the solution was concentrated. The residue is poured onto ice, extracted with ethyl acetate, dried and concentrated. After chromatography on silica gel (cyclohexane/ethyl acetate 1:1), 284 mg (34% of theory) of the desired compound were obtained.

Preparation of (1,3,5,7-tetraoxo-1,3,5,7-tetrahydro-2H,6H-[1,4]dithiino[2,3-c:5,6-c']dipyrrole-2,6-diyl)dipropane-1,2-diyl diacetate [compound No. (36)]

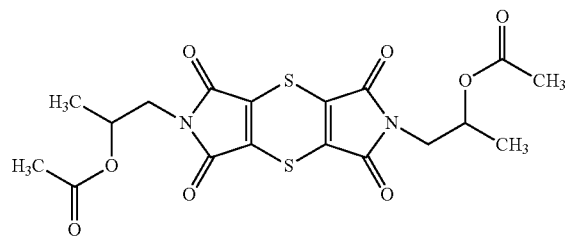 [SMILES: CC(=O)OC(C)Cn1c(=O)c2sc3c(=O)n(CC(C)OC(C)=O)c(=O)c3sc2c1=O]

To a solution of 1.1 g (3.72 mmol) of 1-(3,4-dichloro-2,5-dioxo-2,5-dihydro-1H-pyrrol-1-yl)propan-2-yl acetate in 10 ml of ethanol, there was added 0.283 g (3.72 mmol) of thiourea, and stirring was continued for 5 hours at 40° C. After the mixture has cooled to room temperature, green crystals were filtered off with suction and rinsed with water/ethanol. The filtrate was extracted with water and ethyl acetate, dried and concentrated. The mother liquor was chromatographed on silica gel (cyclohexane/ethyl acetate gradient 0%→100%). This gave 0.334 g (39.5% of theory) of the desired compound.

Preparation of 2,6-dimethyl-1H,5H-[1,4]dithiino[2,3-c:5,6-c']dipyrrole-1,3,5,7(2H,6H)-tetrone 4-oxide [compound No. (38)]

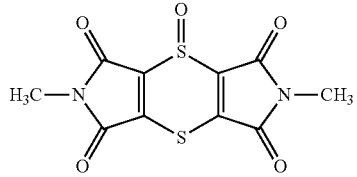

With stirring, 3 g (10.63 mmol) of 2,6-dimethyl-1H,5H-[1,4]dithiino[2,3-c:5,6-c']dipyrrole-1,3,5,7(2H,6H)-tetrone [compound No. (1)] were added to 20 ml of ice-cooled (5° C.) fuming nitric acid. After dissolution was complete, stirring was continued for 5 min, the mixture was subsequently poured into ice-water and the yellow crystals were filtered off with suction. This gave 2.56 g (80.8% of theory) of the desired compound.

The compounds of the formula (I) which are mentioned in Table 1 hereinbelow can be obtained analogously to the above examples and in accordance with the general descriptions of the processes.

TABLE 1

(I)

| No. | $R^1$ | $R^2$ | n | Physical data |
|---|---|---|---|---|
| 1 | Me | Me | 0 | log P = 2.32 |
| 2 | Et | Et | 0 | $^1$H NMR (400 MHz, DMSO-$d_6$): δ = 1.096; 3.442 ppm |
| 3 | nPr | nPr | 0 | $^1$H NMR (400 MHz, DMSO-$d_6$): δ = 0.822; 1.566; 3.362 ppm |
| 4 | iPr | iPr | 0 | log P = 4.19 |
| 5 | cPr | cPr | 0 | $^1$H NMR (400 MHz, DMSO-$d_6$): δ = 0.50-0.89 ppm |
| 6 | —CH$_2$CF$_3$ | —CH$_2$CF$_3$ | 0 | log P = 3.41 |
| 7 | 1-(trifluoromethyl)-cyclopropyl | 1-(trifluoromethyl)-cyclopropyl | 0 | log P = 4.03 |
| 8 | H | H | 0 | log P = 1.13 |
| 9 | 3,5-dichlorophenyl | 3,5-diclorophenyl | 0 | m.p. > 300° C. |
| 10 | Ph | Ph | 0 | m.p. > 300° C. |
| 11 | Bz | Bz | 0 | log P = 4.60 |
| 12 | 2-methoxyethyl | 2-methoxyethyl | 0 | log P = 2.55 |
| 13 | 2-hydroxybutyl | 2-hydroxybutyl | 0 | log P = 2.27 |
| 14 | 2-hydroxypropyl | 2-hydroxypropyl | 0 | log P = 1.63 |
| 15 | 2-phenoxyethyl | -phenoxyethyl | 0 | log P = 3.86 |
| 16 | 2-ethoxyethyl | 2-ethoxyethyl | 0 | log P = 3.24 |
| 17 | 2-phenylpropan-2-yl | 2-phenylpropan-2-yl | 0 | $^1$H NMR (400 MHz, DMSO-$d_6$): δ = 7.20-7.35 ppm |
| 18 | 1-phenylethyl | 1-phenylethyl | 0 | $^1$H NMR (400 MHz, DMSO-$d_6$): δ = 5.197; 5.215; 5.234; 5.251 ppm |
| 19 | 2-methoxy-2-methylpropyl | 2-methoxy-2-methylpropyl | 0 | |
| 20 | tBu | tBu | 0 | |
| 21 | —(CH$_2$)$_2$OC(=O)CH$_3$ | —(CH$_2$)$_2$OC(=O)CH$_3$ | 0 | $^1$H NMR (400 MHz, DMSO-$d_6$): δ = 1.053; 3.654; 4.110 ppm |
| 22 | —C$_6$H$_4$—SO$_2$NH$_2$ | —C$_6$H$_4$—SO$_2$NH$_2$ | 0 | $^1$H NMR (400 MHz, DMSO-$d_6$): δ = 7.492; 7.596; 7.583; 7.946; 7.966 ppm |
| 23 | —CH$_2$CO$_2$H | —CH$_2$CO$_2$H | 0 | $^1$H NMR (400 MHz, DMSO-$d_6$): δ = 4.166 ppm |
| 24 | CH(CH$_3$)CO$_2$H | CH(CH$_3$)CO$_2$H | 0 | log P = 1.76 |
| 25 | CH(CH$_2$CH$_3$)CO$_2$H | CH(CH$_2$CH$_3$)CO$_2$H | 0 | |

TABLE 1-continued (I)

| No. | R¹ | R² | n | Physical data |
|-----|----|----|---|---------------|
| 26 | $(CH_2)_3CH_3$, $CO_2H$ (branched) | $(CH_2)_3CH_3$, $CO_2H$ (branched) | 0 | |
| 27 | $C(CH_3)_3$, $CO_2H$ (branched) | $C(CH_3)_3$, $CO_2H$ (branched) | 0 | $^1$H NMR (400 MHz, DMSO-$d_6$): δ = 1.620 ppm |
| 28 | $CO_2H$, $CH_3$ (branched) | $CO_2H$, $CH_3$ (branched) | 0 | log P = 1.99 |
| 29 | —$(CH_2)_4CO_2H$ | —$(CH_2)_4CO_2H$ | 0 | log P = 2.02 |
| 30 | 3-(trifluoromethyl)-cyclohexyl | 3-(trifluoromethyl)-cyclohexyl | 0 | $^{13}$C NMR (150 MHz, DMSO-$d_6$): δ = 23.01; 23.71; 27.85; 28.61; 49.19; 126.77; 128.62; 130.56; 164.22 ppm |
| 31 | 3-(trifluoromethyl)-phenyl | 3-(trifluoromethyl)-phenyl | 0 | log P = 4.91 |
| 32 | $CO_2H$, benzyl (branched) | $CO_2H$, benzyl (branched) | 0 | log P = 3.12 |
| 33 | 2-hydroxyethyl | 2-hydroxyethyl | 0 | $^1$H NMR (400 MHz, DMSO-$d_6$): δ = 3.480 ppm |
| 34 | 2-hydroxy-2-methylpropyl | 2-hydroxy-2-methylpropyl | 0 | log P = 3.65 |
| 35 | O-$COCH_3$, $CH_3$ (branched) | O-$COCH_3$, $CH_3$ (branched) | 0 | log P = 3.09 |
| 36 | O-$COCH_3$, $CH_3$ (branched) | O-$COCH_3$, $CH_3$ (branched) | 0 | log P = 3.09 |
| 37 | hydroxymethyl | hydroxymethyl | 0 | $^1$H NMR (400 MHz, DMSO-$d_6$): δ = 3.135; 4.789 ppm |
| 38 | Me | Me | 1 | m.p. 205° C. |
| 39 | H | Et | 0 | log P = 2.13 |
| 40 | $(CH_2)_3CH_3$, $CO_2Et$ (branched) | $(CH_2)_3CH_3$, $CO_2Et$ (branched) | 0 | log P = 4.66 |
| 41 | $CH_2CH_3$, $CO_2H$ (branched) | $CH_2CH_3$, $CO_2Et$ (branched) | 0 | log P = 1.73 |

Me = methyl,
Et = ethyl,
nPr = n-propyl,
iPr = isopropyl,
cPr = cyclopropyl,
tBu = teret-butyl,
Bz = benzyl,
Ph = phenyl Preparation of Starting Materials of the Formula (IV)

Preparation of 4-oxo-4-{[1-(trifluoromethyl)cyclopropyl]amino}butanoic acid (IV-1)

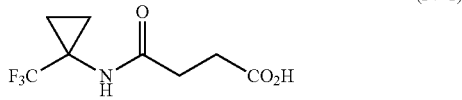

Slowly, 800.7 mg (4.96 mmol) of 1-(trifluoromethyl)cyclopropanamine and 0.85 ml (4.96 mmol) of diisopropylethylamine were added to a solution of 496 mg (4.96 mmol) of succinic anhydride in 10 ml of dioxane, with ice-cooling (10° C.). Stirring was continued for 20 min at room temperature, and the mixture was allowed to stand overnight at this temperature. Again, stirring was continued for 20 min at 80° C., the mixture was allowed to cool to room temperature, and the solution was concentrated. Repeatedly, the solution was washed alternately with ethyl acetate and with water. The combined organic phases were dried and concentrated. This gave 815.8 mg (73% of theory) of the desired compound.

The determination of the log P values detailed in the tables and preparation examples hereinabove is carried out in accordance with EEC Directive 79/831 Annex V.A8 by means of HPLC (High Performance Liquid Chromatography) on a reversed-phase column (C 18). Temperature: 43° C.

The determination is carried out in the acidic range at pH 2.7, using 0.1% strength aqueous formic acid and acetonitrile (contains 0.1% formic acid) as eluents; linear gradient from 10% acetonitrile to 95% acetonitrile.

Calibration is carried out using unbranched alkan-2-ones (with 3 to 16 carbon atoms) with known log P values (determination of the log P values with reference to the retention times by linear interpolation between two successive alkanones).

USE EXAMPLES

Example A

*Phytophthora* Test (Tomato)/Protective

Solvent: 24.5 parts by weight of acetone
    24.5 parts by weight of dimethylacetamide
Emulsifier: 1 part by weight of alkylaryl polyglycol ether To prepare a suitable preparation of active substance, 1 part by weight of active substance is mixed with the stated amounts of solvent and emulsifier, and the concentrate is diluted with water to the desired concentration.

To test for protective activity, young plants are sprayed with the active substance preparation at the application rate detailed. After the spray coating has dried on, the plants are inoculated with an aqueous spore suspension of *Phytophthora infestans*. Then, the plants are placed into an incubation cabinet at approximately 20° C. and 100% relative atmospheric humidity. Evaluation is carried out 3 days after the inoculation. 0% means an efficacy which corresponds to that of the control, while an efficacy of 100% means that no disease is observed.

In this test, the compounds 1, 2 and 3 according to the invention showed an efficacy of 70% or more at an active substance concentration of 250 ppm.

Example B

*Plasmopara* Test (Grapevine)/Protective

Solvent: 24.5 parts by weight of acetone
    24.5 parts by weight of dimethylacetamide
Emulsifier: 1 part by weight of alkylaryl polyglycol ether To prepare a suitable preparation of active substance, 1 part by weight of active substance is mixed with the stated amounts of solvent and emulsifier, and the concentrate is diluted with water to the desired concentration.

To test for protective activity, young plants are sprayed with the active substance preparation at the application rate detailed. After the spray coating has dried on, the plants are inoculated with an aqueous spore suspension of *Plasmopara viticola* and then remain for 1 day in an incubation cabinet at approximately 20° C. and 100% relative atmospheric humidity. Thereafter, the plants are placed for 4 days in the greenhouse at approximately 21° C. and approximately 90% atmospheric humidity. The plants are then moistened and placed for 1 day into an incubation cabinet. Evaluation is carried out 6 days after the inoculation. 0% means an efficacy which corresponds to that of the control, while an efficacy of 100% means that no disease is observed.

In this test, the compounds 1, 2 and 3 according to the invention showed an efficacy of 70% or more at an active substance concentration of 250 ppm.

Example C

*Venturia* Test (Apple)/Protective

Solvent: 24.5 parts by weight of acetone
    24.5 parts by weight of dimethylacetamide
Emulsifier: 1 part by weight of alkylaryl polyglycol ether To prepare a suitable preparation of active substance, 1 part by weight of active substance is mixed with the stated amounts of solvent and emulsifier, and the concentrate is diluted with water to the desired concentration.

To test for protective activity, young plants are sprayed with the active substance preparation at the application rate detailed. After the spray coating has dried on, the plants are inoculated with an aqueous conidia suspension of the apple scab pathogen *Venturia inaequalis* and then remain for 1 day in an incubation cabinet at approximately 20° C. and 100% relative atmospheric humidity. Thereafter, the plants are placed in the greenhouse at approximately 21° C. and approximately 90% relative atmospheric humidity. Evaluation is carried out 10 days after the inoculation. 0% means an efficacy which corresponds to that of the control, while an efficacy of 100% means that no disease is observed.

In this test, the compounds 1, 2 and 3 according to the invention showed an efficacy of 70% or more at an active substance concentration of 250 ppm.

Example D

*Alternaria* Test (Tomato)/Protective

Solvent: 24.5 parts by weight of acetone
    24.5 parts by weight of dimethylacetamide
Emulsifier: 1 part by weight of alkylaryl polyglycol ether To prepare a suitable preparation of active substance, 1 part by weight of active substance is mixed with the stated amounts of solvent and emulsifier, and the concentrate is diluted with water to the desired concentration.

To test for protective activity, young plants are sprayed with the active substance preparation at the application rate detailed. After the spray coating has dried on, the plants are inoculated with an aqueous spore suspension of *Alternaria solani*. Then, the plants are placed into an incubation cabinet at approximately 20° C. and 100% relative atmospheric humidity. Evaluation is carried out 3 days after the inoculation. 0% means an efficacy which corresponds to that of the control, while an efficacy of 100% means that no disease is observed.

In this test, the compounds 1, 2 and 3 according to the invention showed an efficacy of 70% or more at an active substance concentration of 250 ppm.

Example E

Botrytis Test (Cucumber)/Protective

Solvent: 49 parts by weight of N,N-dimethylformamide
Emulsifier: 1 part by weight of alkylaryl polyglycol ether To prepare a suitable preparation of active substance, 1 part by weight of active substance is mixed with the stated amounts of solvent and emulsifier, and the concentrate is diluted with water to the desired concentration.

To test for protective activity, young cucumber plants are sprayed with the active substance preparation at the application rate detailed. One day after the treatment, the plants are inoculated with a spore suspension of *Botrytis cinerea* and are then left to stand for 48 h at 100% relative humidity at 22° C. Thereafter, the plants are left to stand at 96% relative atmospheric humidity and a temperature of 14° C. Evaluation is carried out 5-6 days after the inoculation. 0% means an efficacy which corresponds to that of the control, while an efficacy of 100% means that no disease is observed.

In this test, the compounds 1, 2 and 3 according to the invention showed an efficacy of 70% or more at an active substance concentration of 500 ppm.

Example F

Pyrenophora teres Test (Barley)/Protective

Solvent: 50 parts by weight of N,N-dimethylacetamide
Emulsifier: 1 part by weight of alkylaryl polyglycol ether To prepare a suitable preparation of active substance, 1 part by weight of active substance is mixed with the stated amounts of solvent and emulsifier, and the concentrate is diluted with water to the desired concentration.

To test for protective activity, young plants are sprayed with the active substance preparation at the application rate detailed. After the spray coating has dried on, the plants are sprayed with a spore suspension of *Pyrenophora teres*. The plants remain in an incubation cabinet for 48 hours at 20° C. and 100% relative atmospheric humidity. The plants are placed in a greenhouse at a temperature of approximately 20° C. and a relative atmospheric humidity of approximately 80%.

Evaluation is carried out 8 days after the inoculation. 0% means an efficacy which corresponds to that of the control, while an efficacy of 100% means that no disease is observed.

In this test, the compound 1 according to the invention showed an efficacy of 70% or more at an active substance concentration of 1000 ppm.

The invention claimed is:

1. A method of controlling phytopathogenic fungi, comprising applying a composition comprising at least one compound of formula (I)

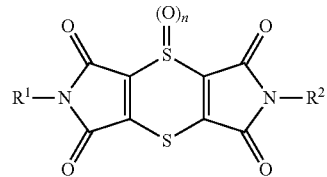

(I)

in which $R^1$ and $R^2$ are identical or different and represent hydrogen; $C_1$-$C_8$-alkyl which is optionally monosubstituted or polysubstituted by halogen, —$OR^3$, or —$COR^4$; $C_3$-$C_7$-cycloalkyl which is optionally monosubstituted or polysubstituted by halogen, $C_1$-$C_4$-alkyl, or $C_1$-$C_4$-haloalkyl; or aryl or aryl-($C_1$-$C_4$-alkyl), each of which is optionally monosubstituted or polysubstituted by halogen, $C_1$-$C_4$-alkyl, $C_1$-$C_4$-haloalkyl, —$COR^4$, or sulphonylamino, $R^3$ represents hydrogen, $C_1$-$C_4$-alkyl, $C_1$-$C_4$-alkylcarbonyl, or represents aryl which is optionally monosubstituted or polysubstituted by halogen, $C_1$-$C_4$-alkyl, or $C_1$-$C_4$-haloalkyl, $R^4$ represents hydroxyl, $C_1$-$C_4$-alkyl, or $C_1$-$C_4$-alkoxy, and n represents 0 or 1.

2. The method of claim 1, wherein $R^1$ and $R^2$ are identical or different and represent hydrogen; $C_1$-$C_6$-alkyl which is optionally monosubstituted or polysubstituted by fluorine, chlorine, bromine, —$OR^3$, or —$COR^4$; $C_3$-$C_7$-cycloalkyl which is optionally monosubstituted or polysubstituted by chlorine, methyl, or trifluoromethyl; or phenyl or phenyl-($C_1$-$C_4$-alkyl), each of which is optionally monosubstituted or polysubstituted by fluorine, chlorine, bromine, methyl, trifluoromethyl, —$COR^4$, or sulphonylamino, $R^3$ represents hydrogen, methyl, ethyl, methylcarbonyl, ethylcarbonyl, or represents phenyl which is optionally monosubstituted or polysubstituted by fluorine, chlorine, methyl, ethyl, n-propyl, isopropyl, or trifluoromethyl, $R^4$ represents hydroxyl, methyl, ethyl, methoxy, or ethoxy, and n represents 0 or 1.

3. The method of claim 1, wherein $R^1$ and $R^2$ are identical or different and represent hydrogen; $C_1$-$C_4$-alkyl which is optionally monosubstituted or polysubstituted by fluorine, chlorine, hydroxyl, methoxy, ethoxy, methylcarbonyloxy, or carboxyl; $C_3$-$C_7$-cycloalkyl which is optionally monosubstituted or polysubstituted by chlorine, methyl, or trifluoromethyl; or phenyl, benzyl, 1-phenethyl, 2-phenethyl, or 2-methyl-2-phenethyl, each of which is optionally monosubstituted to trisubstituted by fluorine, chlorine, bromine, methyl, trifluoromethyl, —$COR^4$, or sulphonylamino, $R^3$ represents hydrogen, methyl, methylcarbonyl, or phenyl, $R^4$ represents hydroxyl, or methoxy, and n represents 0 or 1.

4. The method of claim 1, wherein $R^1$ and $R^2$ simultaneously represent methyl.

5. The method of claim 1, wherein the at least one compound of formula (I) is applied to the fungi, their environment, or a combination thereof.

6. A compound of formula (I-a)

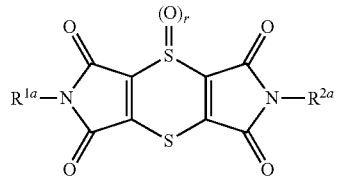

(I-a)

in which $R^{1a}$ and $R^{2a}$ are identical or different and represent $C_1$-$C_8$-alkyl which is monosubstituted or polysubstituted by fluorine, —$OR^{3a}$, or —$COR^{4a}$; $C_3$-$C_7$-cycloalkyl which is optionally monosubstituted or polysubstituted by halogen, $C_1$-$C_4$-alkyl, or $C_1$-$C_4$-haloalkyl; or aryl-($C_1$-$C_4$-alkyl) which is monosubstituted in the alkyl moiety by —$COR^{4a}$, $R^{3a}$ represents $C_1$-$C_4$-alkyl, $C_1$-$C_4$-alkylcarbonyl, or represents aryl which is optionally monosubstituted or polysubstituted by halogen, $C_1$-$C_4$-alkyl, or $C_1$-$C_4$-haloalkyl, $R^{4a}$ represents hydroxyl, $C_1$-$C_4$-alkyl, or $C_1$-$C_4$-alkoxy, and r represents 0 or 1, with the proviso that $R^{1a}$ and $R^{2a}$ do not simultaneously represent acetoxymethyl or methoxymethyl.

7. The compound of claim 6, wherein $R^{1a}$ and $R^{2a}$ are identical or different and represent $C_1$-$C_6$-alkyl which is monosubstituted or polysubstituted by fluorine, —$OR^{3a}$, or —$COR^4$; $C_3$-$C_7$-cycloalkyl which is optionally monosubstituted or polysubstituted by chlorine, methyl, or trifluoromethyl; or phenyl-($C_1$-$C_4$-alkyl) which is monosubstituted in the alkyl moiety by —$COR^{4a}$, $R^{3a}$ represents methyl, ethyl, methylcarbonyl, ethylcarbonyl, or represents phenyl which is optionally monosubstituted or polysubstituted by fluorine, chlorine, methyl, ethyl, n-propyl, isopropyl, or trifluoromethyl, $R^{4a}$ represents hydroxyl, methyl, ethyl, methoxy, or ethoxy, and r represents 0 or 1, with the proviso that $R^{1a}$ and $R^{2a}$ do not represent acetoxymethyl.

8. The compound of claim 6, wherein $R^{1a}$ and $R^{2a}$ are identical or different and represent $C_1$-$C_4$-alkyl which is monosubstituted or polysubstituted by fluorine, hydroxyl, methoxy, ethoxy, methylcarbonyloxy, or carboxyl; $C_3$-$C_7$-cycloalkyl which is optionally monosubstituted or polysubstituted by chlorine, methyl, or trifluoromethyl; or 1-phenethyl or 2-phenethyl, each of which is monosubstituted in the alkyl moiety by —$COR^{4a}$, $R^{3a}$ represents methyl, methylcarbonyl, or phenyl, $R^{4a}$ represents hydroxyl or methoxy, and r represents 0, with the proviso that $R^{1a}$ and $R^{2a}$ do not represent acetoxymethyl.

9. The method of claim 1, wherein the phytopathogenic fungi is selected from the group consisting of *Blumeria* spp., *Podosphaera* spp., *Sphaerotheca* spp., *Uncinula* spp., *Gymnosporangium* spp., *Hemileia* spp., *Phakopsora* spp., *Puccinia* spp., *Uromyces* spp., *Bremia* spp., *Peronospora* spp., *Phytophthora* spp., *Plasmopara* spp., *Pseudoperonospora* spp., *Pythium* spp., *Alternaria* spp., *Cercospora* spp., *Cladiosporum* spp., *Cochliobolus* spp., *Colletotrichum* spp., *Cycloconium* spp., *Diaporthe* spp., *Elsinoe* spp., *Gloeosporium* spp., *Glomerella* spp., *Guignardia* spp., *Leptosphaeria* spp., *Magnaporthe* spp., *Microdochium* spp., *Mycosphaerella* spp., *Phaeosphaeria* spp., *Pyrenophora* spp., *Ramularia* spp., *Rhynchosporium* spp., *Septoria* spp., *Typhula* spp., *Venturia* spp., *Corticium* spp., *Fusarium* spp., *Gaeumannomyces* spp., *Rhizoctonia* spp., *Tapesia* spp., *Thielaviopsis* spp., *Aspergillus* spp., *Cladosporium* spp., *Claviceps* spp., *Fusarium* spp., *Gibberella* spp., *Monographella* spp., *Septoria* spp., *Sphacelotheca* spp., *Tilletia* spp., *Urocystis* spp., *Ustilago* spp., *Botrytis* spp., *Penicillium* spp., *Sclerontinia* spp., *Verticilium* spp., *Sclerotium* spp., *Nectria* spp., *Monilinia* spp., *Taphrina* spp., *Esca* spp., *Helminthosporium* spp., *Xanthomonas* spp., *Pseudomonas* spp., and *Erwinia* spp.

10. The method of claim 1, wherein the phytopathogenic fungi is selected from the group consisting of *Phytophthora* spp., *Plasmopara* spp., *Alternaria* spp., *Pyrenophora* spp., *Venturia* spp., and *Botrytis* spp.

11. The method of claim 1, wherein the compound is

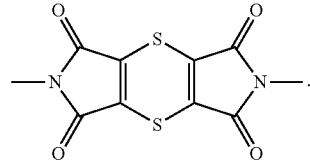

* * * * *